United States Patent [19]
Zweig

[11] Patent Number: 4,647,430
[45] Date of Patent: Mar. 3, 1987

[54] VOLUME INDEPENDENT TEST DEVICE

[75] Inventor: Stephen E. Zweig, South Bend, Ind.

[73] Assignee: Miles Laboratories, Inc., Elkhart, Ind.

[21] Appl. No.: 746,767

[22] Filed: Jun. 20, 1985

[51] Int. Cl.[4] .................. G01N 31/22; G01N 33/52; G01N 33/53

[52] U.S. Cl. .................. 422/56; 422/58; 435/805

[58] Field of Search .............. 422/56, 57, 58; 435/805; 436/169, 170

[56] References Cited

U.S. PATENT DOCUMENTS

| | | | |
|---|---|---|---|
| 3,798,004 | 3/1974 | Zerachia et al. | 422/56 |
| 4,144,306 | 3/1979 | Figueras | 422/56 |
| 4,160,008 | 7/1979 | Fenocketti et al. | 422/56 |
| 4,256,693 | 3/1981 | Kondo et al. | 422/57 X |
| 4,258,001 | 3/1981 | Pierce et al. | 436/170 X |
| 4,518,565 | 5/1985 | Boger et al. | 422/61 X |
| 4,551,306 | 11/1985 | Bouwman et al. | 422/56 |
| 4,562,148 | 12/1985 | Sommer | 422/56 X |

FOREIGN PATENT DOCUMENTS

| | | |
|---|---|---|
| 2170397 | 8/1973 | France . |
| 1349623 | 4/1974 | United Kingdom . |
| 1369139 | 10/1974 | United Kingdom . |

Primary Examiner—Barry S. Richman
Assistant Examiner—Jill Johnston
Attorney, Agent, or Firm—Roger N. Coe

[57] ABSTRACT

A volume independent test device is formed in which the reagent matrix is covered by a water-impermeable coating or membrane. At least three openings extend through the coating or membrane material, penetrating into the underlying reagent matrix. These openings permit liquid to pass through the coating or membrane material and into the reagent matrix material until the reagent matrix becomes saturated.

10 Claims, 4 Drawing Figures

VOLUME INDEPENDENT TEST DEVICE

FIELD OF THE INVENTION

The present invention relates to volume independent test devices and, more particularly, the present invention relates to method of forming a volume independent solid state test strip by covering the top of the reagent matrices with a water impermeable or semipermeable coating or membrane having spaced openings of limited size which permit liquid to pass through the coating or membrane and contact the underlying reagent matrix until the matrix becomes saturated.

BACKGROUND OF THE INVENTION

The art of analytical chemistry has been greatly advanced since biochemistry began emerging as a primary scientific frontier, requiring increasingly sophisticated analytical methods and tools to solve problems. Likewise the medical profession has lent impetus to the growth of analytical chemistry, with its desiderata of both high precision and speed in obtaining results.

To satisfy the needs of the medical profession as well as other expanding technologies, such as the brewing industry, chemical manufacturing, etc., a myriad of analytical procedures, compositions and apparatus have evolved, including the so-called "dip-and-read" type reagent test device. Reagent test devices enjoy wide use in many analytical applications, especially in the chemical analysis of biological fluids, because of their relatively low cost, ease of use, and speed in obtaining results. In medicine, for example, numerous physiological functions can be monitored merely by dipping a reagent strip test device into a sample of body fluid, such as urine or blood, and observing a detectable response, such as a change in color or a change in the amount of light reflected from or absorbed by the test device.

Many of the "dip-and-read" test devices for detecting body fluid components are capable of making quantitative or at least semiquantitative measurements. Thus, by measuring the response after a predetermined time, an analyst can obtain not only a positive indication of the presence of a particular constituent in a test sample, but also an estimate of how much of the constituent is present. Such test devices provide the physician with a facile diagnostic tool as well as the ability to gauge the extent of disease or of bodily malfunction.

Illustrative of such test devices currently in use are products available from the Ames Division of Miles Laboratories, Inc. under the trademarks CLINISTIX, MULTISTIX, KETOSTIX, N-MULTISTIX, DIASTIX, DEXTROSTIX, and others. Test devices such as these usually comprise one or more carrier matrices, such as absorbent paper, having incorporated therein a particular reagent or reactant system which manifests a detectable response, e.g., a color change, in the presence of a specific test sample component or constituent. Depending on the reactant system incorporated with a particular matrix, these test devices can detect the presence of glucose, ketone bodies, bilirubin, urobilinogen, occult blood, nitrite, and other substances. A specific change in the intensity of color observed within a specific time range after contacting the test device with a sample is indicative of the presence of a particular constituent and/or its concentration in the sample. Some of these test devices and their reagent systems are set forth in U.S. Pat. Nos. 3,123,443; 3,212,855 and 3,814,668.

Thus, it is customary for reagent test devices to contain more than one reagent bearing carrier matrix, in which each reagent bearing carrier matrix is capable of detecting a particular constituent in a liquid sample. For example, a reagent test device could contain a reagent bearing carrier matrix responsive to glucose in urine and another matrix responsive to ketones, such as acetoacetate, which is spaced from, but adjacent to, the glucose responsive matrix. Such a product is marketed by the Ames division of Miles Laboratories, Inc. under the trademark KETO-DIASTIX. Another reagent test device marketed by the Ames Division of Miles Laboratories, Inc., N-MULTISTIX, contains eight adjacent reagent incorporated matrices providing analytical measurement of pH, protein, glucose, ketones, bilirubin, occult blood, nitrite, and urobilinogen.

For some assays it has been found that test devices cannot be used in the normal way by simply dipping the test device into a sample or solution to be measured. For such assays the amount or volume of the sample which contacts the reagent test device is very critical and for such assays a very precise amount of sample must be applied to the reagent matrix each time an assay is performed in order to achieve consistent results. For such assays the development of a volume independent test device in which the amount of sample which comes in contact with the reagent matrix remains constant each time an assay is used would be extremely important since it would overcome problems of inconsistent results due to differences in the amount of sample contacted with the reagents in a matrix. The present invention is primarily directed to achieving constant sample loading per unit area of a reagent matrix and thus a truly volume independent test device.

SUMMARY OF THE INVENTION

An object of the present invention is to provide a volume independent test device.

Another object of the present invention is to provide test devices in which a constant sample loading per unit area can be achieved.

Still another object of the present invention is to provide a method of producing a volume independent solid phase test device.

In accordance with the present invention, the reagent matrix of a conventional dip-and-read test device is covered on at least its top surface with a water impermeable or semipermeable coating or membrane having in excess of three openings which permit liquid to pass through said membrane to the underlying reagent matrix until said matrix becomes saturated. The percentage of the surface area taken up by the openings can range from a lower limit of about 0.01 percent to an upper limit of about 5 percent.

In use the amount of sample applied to the exposed surface of the coating or membrane becomes unimportant. Sample placed on said coating or membrane passes through the openings until the underlying reagent matrix pad is saturated. Upon pad saturation, the remainder of the sample remains on top of the coating or membrane and is prevented from reacting with reagents in the matrix pad, the coating or membrane thus effectively becoming a barrier to further contact between remaining applied sample and components of the reagent matrix. Accordingly, the resulting test device achieves constant loading of sample per unit area regardless of the amount of sample applied to the test device and a volume independent test device is obtained.

The volume independent test devices of the present invention and the process for forming such test devices are suited to a broad range of volume sensitive solid phase test devices which are based primarily on absorbent matrices such as paper. These include assays for glucose, AST (cholesterol), ALT (phenobarital), theophylline and other immunochemical assays.

BRIEF DESCRIPTION OF THE DRAWINGS

Other and further objects, advantages and features of the invention will be apparent to those skilled in the art from the following detailed description thereof, taken into conjunction with the following drawings in which.

DESCRIPTION OF THE PREFERRED EMBODIMENTS

Figure 1:
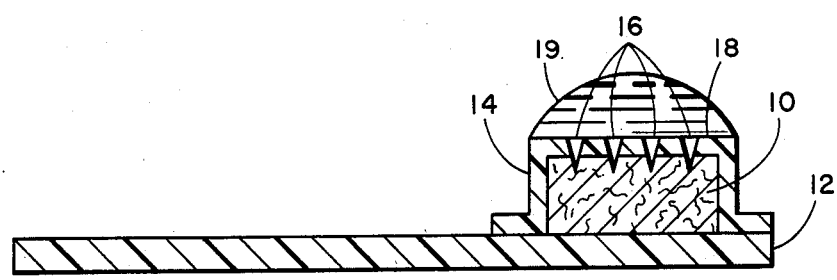
FIG. 1 is a diagrammatic side view, in cross-section, of a test device illustrating an embodiment in accordance with the present invention.
Figure 2:
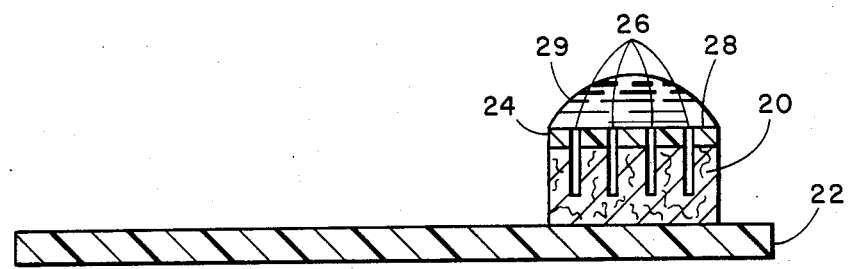
FIG. 2 is a diagrammatic side view, in cross-section, illustrating another embodiment of a test device in accordance with the present invention.

Referring to the drawings, test devices in accordance with the present invention are illustrated in FIGS. 1 and 2. These figures illustrate reagent test devices which comprise reagent matrix areas attached to a substrate. The reagent pad or matrix material 10 (in FIG. 1) and 20 (in FIG. 2) can be formed from any suitable material. U.S. Pat. No. 3,846,247, for example, teaches the use of felt, porous ceramic material and woven or matted glass fibers. Additionally, U.S. Pat. No. 3,552,928 teaches the use of wood, cloth, sponge material and argillaceous substances. The use of synthetic resin fleeces and glass fiber felts as carrier matrix is suggested in British Pat. No. 1,369,139. Another British Pat. No. 1,349,623, proposes the use of light permeable meshwork of thin filaments as a cover for an underlying paper matrix. Polyimide fibers are taught in French Pat. No. 2,170,397. Notwithstanding these suggestions, however, the material predominantly used in the art as a carrier matrix and that which is especially useful in the present invention is bibulous paper, such as filter paper.

The reagent system which is present depends on the particular analyte to be measured and is within the skill of those in the art. Normally the reagents are impregnated into the carrier matrix prior to the attachment of the carrier matrix to a suitable substrate material.

The substrate (12 in FIG. 1 and 22 in FIG. 2) can be formed from any suitable material such as cellulose acetate, polyethylene, terephthalate, polycarbonate and polystyrene. In the embodiments illustrated in FIGS. 1 and 2 substrates 12 and 22 extend for some distance beyond the overlying reagent matrix area 10 and 20, respectively. This permits an end of the test device opposite that containing the reagent matrix to be used as a handle for convenience in performing an assay. In a preferred embodiment the reagent matrix (10 and 20) is attached to a substrate 12 and 22, respectively, which is composed of polystyrene (TRYCITE, available from Dow Chemical Company) using double faced adhesive tape known as Double Stick, available from the 3M Company.

Covering the top and opposite ends of reagent matrix 10 in FIG. 1 is a coating or membrane 14 which is either impermeable to aqueous fluids or semipermeable. This coating or membrane 14 actually adheres to not only the reagent matrix 10 but also substrate 12 and can be used to maintain reagent matrix 10 in place attached to substrate 12. Coating or membrane 14 normally has a thickness ranging from about 0.005 mm (millimeters) to about 2 mm and preferably from 0.1 mm to 1 mm. The membrane is preferably made of a transparent or translucent material. However, if readings are taken from the bottom of the test device through the support material 12 then the overcoat layer or membrane 14 can be opaque. Suitable transparent or semitransparent materials for membrane 14 include gelatin coatings, Scotch Tape, polyethylene, waxes plastics, silicone, rubber, etc.

Waxes which are especially useful for use as an overcoat barrier layer are those which are thermoplastic, water repellent, smooth in texture, nontoxic and have freedom from any objectionable odor or color. Major types of waxes which can be employed include natural waxes, such as animal wax, beeswax, spermaceti, lanolin, shellac wax; vegetable waxes, such as carnauba, candelilla, bayberry, sugar cane; mineral waxes, such as fossil or earth waxes, including ozocerite, ceresin, montan; and petroleum waxes, such as paraffin, microcrystalline, petrolatum; as well as synthetic waxes such as ethylenic polymers and polyolether-esters including CARBOWAX, sorbitol and chlorinated napthalenes such as HALOWAX and other hydrocarbon waxes. A preferred wax is the WW0404 wax from H. B. Fuller Company of Kalamazoo, Mich., which has the following characteristics: Melting point (ASTM D127) 82° C.±4%, hydrophobic, inert, bendable and not tacky when dry. The congeal point (ASTM D938) is 76° C.±4%, viscosity (Brookfield Thermocal) is 17.5 cps 93° C., and color (ASTM D1500) is 1.0 Saybolt.

Gelatins which are especially useful for use as an overcoat barrier layer are those with small pore size to hinder diffusion to the maximal extent possible. Skin, bone, acid and alkaline processed gelatin from a variety of sources can be used. These include, but are not limited to, AGEA H9, AGEA H7/8 and AGEA 2KN-407 (available from Bayer AG) and Fisher gelatin. Small pore size is generally obtained by using gelatin concentrations in the the 5-20 percent range and by using 1 percent or more of crosslinkers such as XAMA-7 (Cordova Chemical Company, North Muskegon, Michigan), AGFA SOB-2402, methoxyethyl-bisvinylsulfone and other protein crosslinking agents.

Any conventional coating methods can be employed to apply coating or membrane 19 including direct and indirect gravue coating, transfer coating, and other coating methodologies which will produce coatings of the desired thickness and other characteristics mentioned. If the coating or membrane 14 does not readily adhere to matrix 10 (or substrate 12, in the case of FIG. 1) various adhesives can be applied to join membrane 14, matrix 10 and/or substrate 12 together.

For conventionally dimensioned reagent test devices the dimensions of surface 18 of coating or membrane 14 will normally be 0.5 by 1 cm. Surface 18 will contain from 3 to about 300 holes, approximately the size of pin holes in either a regular or irregular spaced configuration such that the holes or openings 16 are fairly uniformly distributed across the total area of the upper surface 18 of membrane 14. Preferably, the number of holes is in the order of magnitude of 30 and these holes, which can have a diameter from 0.1 mM to 1 mM, and, in total, occupy from about 0.01 percent to about 5 percent and generally around 1 percent of the total surface area of surface 18. These openings permit sample liquid 19 to flow through membrane or coating 14 into reagent matrix 10 until the reagent matrix becomes saturated.

The number of holes extending through the overcoat can thus be varied within certain limitations. If the density of the holes is too few then sample will penetrate into the reagent matrix at too low a rate and if the density of the openings is too high then the penetration into the reagent matrix area could prevent the overcoat from acting as a barrier once the reagent matrix becomes saturated and therefore defeat the purpose of the separation.

It has been demonstrated that it is essential to have the holes extending through the coating or barrier material also extend into the reagent matrix material for some distance. Normally, penetration in the range of from 10 percent to 100 percent and preferably from 20 percent to 50 percent into the reagent matrix area is sufficient. Unless the holes penetrate not only the overcoat but also penetrate slightly into the reagent matrix essentially no sample take-up is possible. This means that normally the overcoat will be applied to the reagent matrix and then the holes are formed so as to penetrate the overcoat into the reagent matrix material.

Typically about 30 microliters of sample 19 is applied to a test device in accordance with the present invention and the reagent pad or matrix absorbs 20 to 25 microliters of sample. Openings 16 combined with the absorbent material comprising reagent matrix 10 create a wicking action which serves as the driving force for the transport of sample 19 into reagent matrix 10 through opening 16. This wicking action acts to quickly pull sample through the holes until the matrix 10 is saturated. Once the matrix is saturated the wicking action stops since there is no driving force to cause sample to flow through the holes and excess sample remains on top of membrane 14 isolated from the reagents in matrix 10 by the barrier imposed by membrane 14.

Thus, in accordance with the present invention the amount of sample placed onto the reagent test device is in excess of that required to saturate the reagent pad. When the reagent pad becomes saturated further flow of sample stops and the remainder of the sample remains separated from the reagent pad by the membrane or coating layer and does not thereby affect the reaction.

As seen in FIG. 2 it is not necessary for the membrane or coating on top of the reagent matrix area 20 to actually cover one or more sides of the matrix material. In FIG. 2 reagent matrix 20 is attached to substrate 22 and the overcoat layer 24, ranging from 0.005 millimeters to about 2 millimeters in thickness and preferably from between about 0.01 mm and about 1 mm thickness, covers just the top surface of reagent matrix area 20. The openings 26 in layer 24, similar to openings 16 in FIG. 1, take up an area ranging from about 0.01 to about 5 percent of the total surface 28 of membrane 24. The configuration of the openings 26 in FIG. 2 differ slightly from the V-shaped openings 16 illustrated in FIG. 1. Notwithstanding, as in FIG. 1 the same volume independency is achieved when sample 29 is applied to the top surface 28 of the resulting reagent test device of FIG. 2. When reagent matrix 20 becomes saturated layer 24 acts as a barrier which prevents any further sample 29 from contacting reagent matrix 20.

The volume independent test devices of the present invention can be formed by any suitable method with the openings 16 and 26 formed in the covering film or membrane layer either before or after (but normally after) membranes 14 and 24 have been applied to cover the top of reagent matrix areas 10 and 20, respectively. For example, one procedure for forming the test devices of the present invention is to apply a coating over the reagent matrix areas and then subject the coating to a roller having a series of needles arranged in a set pattern which cause penetration of the coating and the underlying matrix material to achieve openings ranging from about 0.01 to about 5 percent of the total surface area covering the reagent matrices.

As previously indicated, the openings occupy only a small portion of the total surface area with the number of openings ranging from about 3 to about 300. Typically 10 to 50 openings are present and are of such a size that the openings prevent liquid from flowing through without a driving force in addition to gravity. The size of the openings thus is such that the surface tension prevents liquid from flowing through the holes unless a driving force caused by the wicking action of the underlying reagent matrix brings about the transfer of fluid from the surface of the overcoat into the reagent matrix area.

Accordingly, the present invention distinguishes over prior art, including U.S. Pat. No. 3,802,842 which describes a test device having meshwork employed to hold the reagent matrix in place and protect it since, as indicated in that patent, the open surface of the meshwork ranges from 30 to 80 percent of the total surface area and the meshwork does not and can not serve as a barrier by which a volume independent test device is formed. The number, size, extent and purpose of the openings are diametrically opposed to the concept of a sample barrier.

The present invention also differs from devices such as those disclosed in U.S. Pat. No. 3,690,836 which are used primarily for studying biological reactions. These devices comprise a sandwich of sheets sealed together with one opening for the introduction of the biological material into the sealed chamber and another opening to permit the escape of air.

The present invention also differs from multi-layered test devices which incorporate filtering layers and/or spreading layers into the structure, such as set forth in U.S. Pat. No. 4,256,693. The normal spreading layer of such devices is completely porous and is designed to facilitate the introduction of and spreading of sample throughout the reagent matrix uniformly. Accordingly, the spreading layer does not and could not act as a barrier layer.

The following Examples are given for the purpose of illustrating the present invention.

EXAMPLE I

Whatman 31-ET paper was impregnated with chemical components for an enzymatic hexokinase based test for serum glucose, as set forth in C. Wilsey, E. Kurchacova, R. Ide, "A Solid-Phase Reagent Strip Test for the Colorimetric Determination of Serum Glucose on the SERALYZER ® Reflectance Photometer" *Clinical Chemistry*, Vol. 30, No. 6, p. 969 (1984) and the paper was then dried. After drying, the paper was coated with a 10 percent gelatin - 1 percent XAMA (cross-linker from Cordova Chemical Company, NOrth Muskegon, Michigan) layer using a Number 34 Meyer Rod and indirect transfer coating. After the coating had hardened the surface was perforated with 0.25 mm (10 mil) diameter wires to create a regular array of pin holes with 1.6 mm (1/16th inch) spacing between the holes. The resulting reagent matrix material, covered with its overcoat, was then applied to Trycite using double stick adhesive and the resulting reagent cards were slit into test strips by conventional means.

Figure 3:
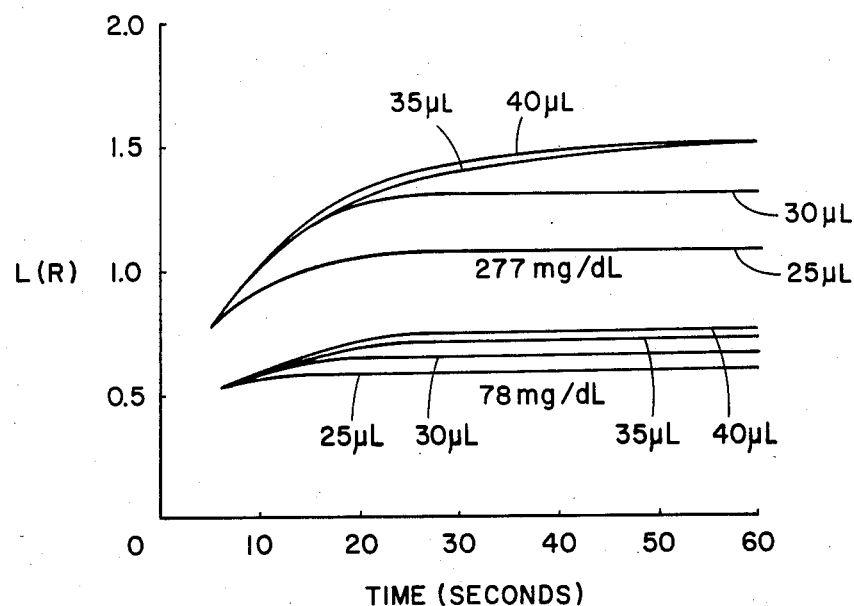
FIG. 3 is graph depicting the performance of a normal hexokinase glucose test device of the prior art.
Figure 4:
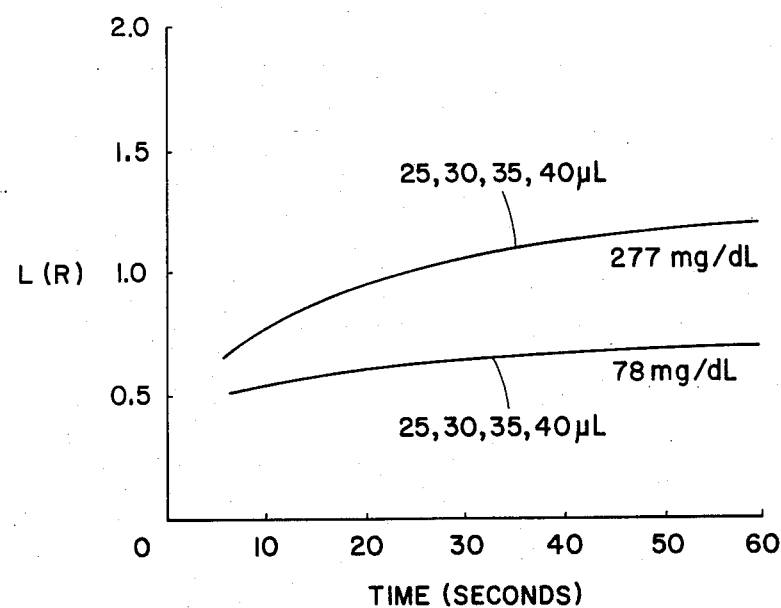
FIG. 4 is a graph illustrating the performance of a volume independent hexokinase test device in accordance with the present invention.

FIGS. 3 and 4 compare the strip performances between a normal hexokinase glucose test strip (FIG. 3) of the prior art and a volume independent hexokinase glucose test strip made in accordance with this Example (FIG. 4). Each test device was given a low [78 milligrams per deciliter (mg/dl)] and a high (277 mg/dl) concentration of glucose in 25 microliters, 30 microliters, 35 microliters and 40 microliters sample volumes. The reflectivities of the resulting test devices were then observed every 5 seconds using a Seralyzer ® photometer available from the Ames Division of Miles Laboratories, Inc., making the readings at 620 nanometers. The test strip reflectivities (R) were converted to a linear function of sample concentration L(R) by applying the following formula:

$$L(R) = \frac{0.57986}{R + 0.16498}$$

As seen from FIG. 3, the reaction profiles of normal hexokinase glucose test devices vary greatly. By contrast, there is almost no variation in the reactivities of the volume independent glucose test devices over the 60 seconds of the assay.

Thus, the performance of the test device of this example is effectively volume independent between the 25 to 40 microliter sample range over the course of one minute. The presence of excess material on top of the reagent matrix can be minimized optically by using an integrating sphere or, alternatively, excess sample can be wiped off and the test device observed visually or instrumentally, with or without an integrating sphere. Accordingly, the present invention removes one of the major problems involved in using test devices which are volume dependent. Even with automated pipetting it is extremely difficult to obtain complete and consistent pipetting of material and these problems are compounded when manual pipetting is attempted. Test devices in accordance with the present invention are especially desired for end point assays since rate tests are nearly volume independent.

From the foregoing, it will be seen that this invention is well adapted to attain all of the ends and objects hereinabove set forth, together with other advantages which are obvious and inherent to the system. The volume independent test device of the present invention is easy to use and easy to prepare. In use, an operator does not have to be precise in the amount of sample applied to the test device. Moreover, it is not necessary to use calibrated pipettes to apply sample to the test devices. Any system capable of applying sample to the test device, including eye droppers, can be employed. The only requirement is that more sample be applied than is required to saturate the pad or the reagent matrix. Normally, the pad or reagent matrix becomes saturated within seconds. Thus, the present invention has the advantages of convenience, simplicity, relatively inexpensiveness, positiveness, effectiveness, durability, accuracy and directness of action. The invention substantially overcomes problems associated with end point assays and other volume dependent tests by removing a problem which has existed for a long period time in connection with solid state test devices. The invention provides a very effective, simple and inexpensive way of eliminating the volume dependency of such test devices. Moreover, the present invention provides a method of performing volume independent test devices which is compatible with existing techniques and methods for forming reagent test devices. It will be apparent that even though only one reagent matrix is shown in FIGS. 1 and 2, test devices could be formed in accordance with the present invention which have multiple reagent matrices present on the same substrate.

Obviously, many other modifications and variations of the invention as hereinbefore set forth can be made without the departing from the spirit and scope thereof, and therefore only such limitations should be imposed as are indicated by the appended claims.

What is claimed is:

1. A volume independent test device comprising a reagent matrix covered by an adhering layer having means defining at least three openings extending through said adhering layer and penetrating into the underlying reagent matrix which permit liquid to pass through said adhering layer into the reagent matrix material until the reagent matrix becomes saturated, said adhering layer being positioned to cover all of the liquid contacting surface of said reagent matrix and being constructed of a material which is impermeable or semipermeable to liquid.

2. The test device of caim 1 in which the number of openings range from about 3 to about 300.

3. The test device of claim 1 in which the number of openings range from about 10 to about 50.

4. The test device of claim 1 in which the percentage of surface area occupied by said openings ranges from about 0.01 to about 5 percent.

5. The test device of any of claims 1 to 4 in which the diameter of the openings is from about 0.01 to about 1 mm.

6. The test device of any of claims 1 to 4 in which the openings extend from about 10 percent to about 100 percent into the underlying reagent matrix.

7. The test device of any of claims 1 to 4 in which the adhering layer has a thickness of from about 0.005 to about 2 mm.

8. A volume independent test device comprising at least one reagent matrix composed of a bibibulous material covered by a membrane containing means defining openings which occupy from about 0.01 percent to about 5 percent of the total area on the top surface of said membrane and in which said openings extend through said membrane and a distance of 10 to 100 percent into said bibulous material, said membrane being positioned to cover all of the liquid contacting surface of said bibulous material and said membrane being impermeable or semipermeable to liquid.

9. A test device comprising a reagent matrix covered by an adhering layer having means defining openings which occupy from about 0.01 percent to about 5 percent of the total surface area of the top surface of said adhering layer and in which the openings extend through said adhering layer and a distance of 10 to 100 percent into said reagent matrix thereby obtaining a test device capable of constant sample loading per unit area of reagent matrix, said adhering layer being positioned to cover all of the liquid contacting surface of said reagent matrix and being constructed of a material which is impermeable or semipermeable to liquid.

10. The test device of any of claims 1 to 4, in which said means defining at least three openings permits only 20 to 25 microliters of liquid to pass through the adhering layer to the underlying reagent matrix.

* * * * *